United States Patent [19]

Eugenio

[11] 4,052,978
[45] Oct. 11, 1977

[54] ELECTRO-THERAPY APPARATUS
[76] Inventor: Amado Eugenio, 2675 Zamora St., Pasay City, Philippines
[21] Appl. No.: 650,234
[22] Filed: Jan. 19, 1976
[30] Foreign Application Priority Data
   Jan. 23, 1975   Philippines ............................... 16736
[51] Int. Cl.$^2$ .......................... A61B 5/05; A61H 39/00
[52] U.S. Cl. ............................... 128/2.1 Z; 128/2.1 C; 128/419 R
[58] Field of Search ............ 128/2.1 C, 2.1 Z, 2.1 R, 128/2.1 M, 419 R

[56]           References Cited
          U.S. PATENT DOCUMENTS

| | | | |
|---|---|---|---|
| 2,736,313 | 2/1956 | Mathison | 128/2.1 Z |
| 2,799,269 | 7/1957 | Mathison | 128/2.1 Z |
| 3,207,151 | 9/1965 | Takagi | 128/2.1 R |
| 3,648,686 | 3/1972 | Payne | 128/2.1 Z |
| 3,894,532 | 7/1975 | Morey | 128/2.1 Z |
| 3,900,020 | 8/1975 | Lock | 128/2.1 C |
| 3,901,214 | 8/1975 | Taaffe | 128/2.1 Z |
| 3,971,366 | 7/1976 | Motoyama | 128/2.12 |

FOREIGN PATENT DOCUMENTS

| | | | |
|---|---|---|---|
| 997,670 | 7/1965 | United Kingdom | 128/2.1 R |

Primary Examiner—Robert W. Michell
Assistant Examiner—Lee S. Cohen
Attorney, Agent, or Firm—Michael J. Striker

[57]           ABSTRACT

This apparatus is an electronically operated device that is transistorized and working generally as an oscillator having a basic oscillation frequency ranging from 50 to 70 cycles per second. Attached to the output terminal of said device is a pair of electrodes that are adapted to be placed on the surfaces of the human body in order to detect the malfunctioning organ or organs of the body through the autonomous nerve systems and for stimulating body organs by way of the acupoints on the body. The pair of electrodes are placed in electrical series with a voltage divider resistor that supplies the bias voltage for the triggering circuit of the oscillator. The detection of the body organs malfunctioning is done by locating a point on the body surfaces wherein the excitation of the sympathetic nerves of the skin will cause depolarization resulting in the increase of conductivity of any particular point in the skin. The indicator of the meter will reveal the malfunctioning organ in accordance with the meridian at which the electro permeable points or acupoints was discovered.

4 Claims, 4 Drawing Figures

FIG. 3
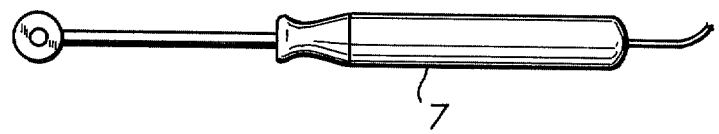
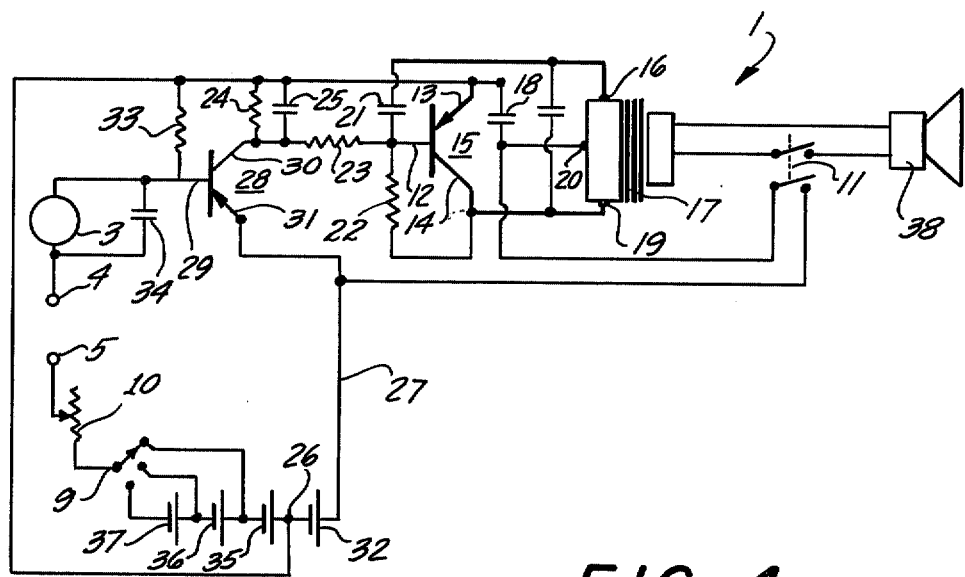
FIG. 4

ELECTRO-THERAPY APPARATUS

SCIENTIFIC BASIS

Based on reflexology, all reflexes of the autonomous nerve system control all functions required of a human body. The majority of diseases are caused by the abnormal functioning of the autonomous (independent) nerves. This is evidenced by the presence of natural negatively charged electrons (electrically charged particles) in the cells of the body. These rtiny invisible electrons are non-organic and non-dissipating with an extraordinary ability to exist in a state of suspended animation in the cells of the body. When excitation of the sympathetic nerves of the skin is made it will cause depolarization resulting in increased conductivity of any particular point in the skin. This electrical resistance found along the meridians (energy vessels) of the body surface is called the electro permeable points or acupoints. The indicator of the ammeter will reveal the malfunctioning organ in accordance with the meridians at which the acupoint was discovered.

ACCOMPLISHMENT OF THE DEVICE

This electro therapy apparatus influences the circulatory system, metabolism, glandular activities, muscular activities, secretion of digestive juices of the internal organs and principally the nerve system of the body. The device can indicate if one is sick or not, can tell what organs are malfunctioning, can stop illness before it can start and become serious, can increase the power of the body to recuperate and help regenerate tissues, can promote normal distribution of energy, blood and nutrients to organs of the body and can stop pains.

OBJECTIVES

The primary object of this invention is to provide a simple electronic device that can detect malfunction of the body organs.

Another object is to provide a device that can stimulate the tissues and organs of the body.

A further object is to provide a transistorized electro-therapy apparatus that can locate and at the same time stimulate the malfunctioning organs of the body.

Still another object is to provide a transistorized circuit that employs a simple oscillator circuit and utilizes the biasing network to supply the detecting and stimulating current to a pair of electrodes.

Other objects and advantages will be well understood upon reading the following specification taken in conjunction with the accompanying drawings.

THE DRAWINGS

FIG. 3 is a perspective view of the searching electrode; and

FIG. 4 is a electrical schematic diagram of the electro-therapy device of this invention.

DESCRIPTION OF THE PANEL

Figure 1:
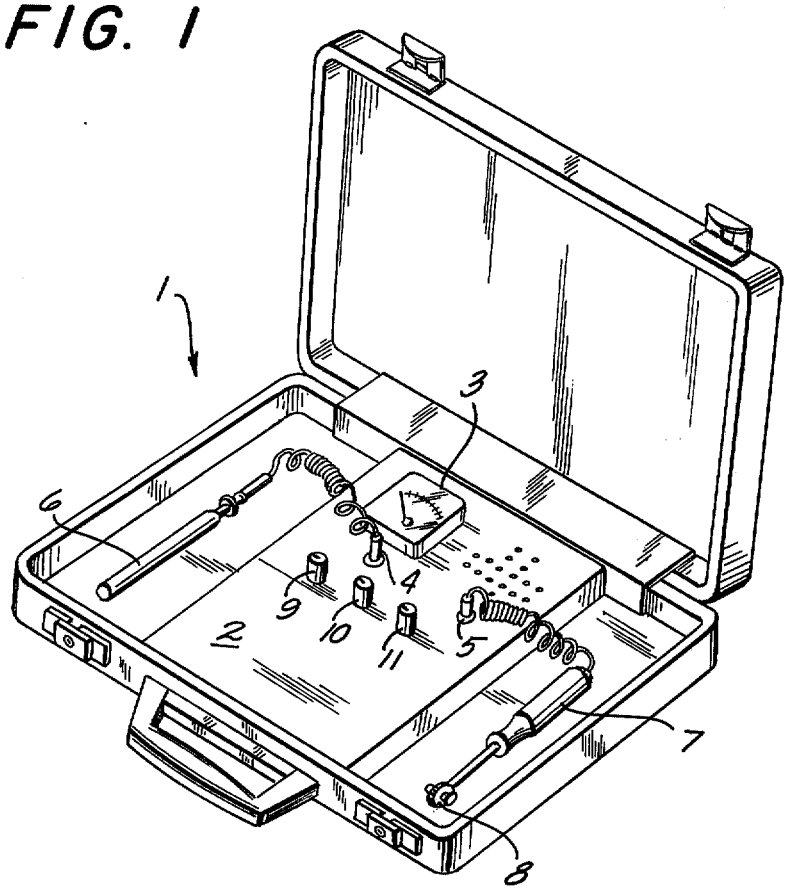
FIG. 1 is a perspective view of the electro-device therapy of this invention.
Figure 2:
FIG. 2 is a perspective view of the grounding electrode.

On the panel 2 of the electro-therapy apparatus 1 contained within a folding suitcase is a small ammeter 3 with a current range of 0 to 500 microamperes. Below the ammeter 3 is a red socket 4 and on the right is a black socket 5. The red plug of the terminal electrode 6 is inserted into the red socket 4 and the black plug of handle 7 of the searcher electrode 8 is inserted into the black socket 5.

Below the sockets 4 and 5 are three knobs. On the left is the voltage control knob 9 which can select a voltage of 6 volts, 12 volts or 21 volts. In the middle is a current control regulator knob 10. On the right is the sound volume control knob 11.

DESCRIPTION OF THE CIRCUIT

The output-oscillator stage is controlled by a simple transistor 15 having a base electrode 12, an emitter electrode 13 and a collector electrode 14. To the collector 14 terminal is connected one end 19 of a push-pull output transformer 17 while the center-tap 20 is connected to the emitter 13 by way of capacitor 18. The other end 16 is connected to the base electrode 12 by way of capacitor 12. The base 12 is coupled to the end 19 of the output transformer 17 by means of resistor 22. The resistors 23 and 24, which latter is by-passed by capacitor 25 are also connected to the base 12. The supply voltage negative terminal 26 is connected to the emitter electrode 13 while the positive terminal 27 connected to the center tap of the output transformer. The biasing network for the oscillator output stage is therefore directly controlled by one side of the primary coil of the output transformer and the resistors 22, 23 and 24. The feed-back voltage being supplied by the other side of primary coil of the output transformer and the coupling capacitor 21. Attached to the output stage is another stage which is adapted to trigger said output stage to cut-off by way of the biasing network of said output stage.

The triggering stage is controlled by a transistor 28 having a base 29, a collector 30 being connected to the negative terminal 26 by way of resistor 24, which is also the biasing network for the output stage, and the emitter 31 is connected directly to the positive terminal 27 of the battery 32 whose output is 9 volts. The biasing network for the triggering stage is controlled by resistor 33 which is connected to the negative side 26 of the battery 32, thru the base 29, then capacitor 34, the pair of electrodes 6 and 8, the rheostat 10, the voltage selector switch 9 and lastly to the negative side of any of the batteries 35, 36 and 37. Placed in parallel with the capacitor 34 is the ammeter 3 which is adapted to record the current supplied to the triggering transistor 28. The battery 32 which supplies the necessary voltage to the output stage is controlled by an "OFF" and "ON" switch 11 and likewise the cutting "in" and "out" of the loudspeaker 38.

As can be seen from the diagram, the pair of electrodes 6 and 8 are in series with the bias voltage dividing network of the triggering transistor 28. By this connection the resistance of the human body, as for example 40,000 ohms, will affect the voltage that will be supplied to the base of the transistor 28. If the pair of electrodes are not connected to the human body the whole apparatus will oscillate with a basic frequency of 50 cycles per second to 70 cycles per second. However, when the electrodes are connected to a resistance that is lower in value the oscillator will oscillate at a frequency higher than the basic flow and flow of current will be visible on the ammeter 3. Points of the body having electro-permeable behavior will show higher flow of current and such increase in current intensities will indicate what organ of the body is malfunctioning. Without the presence of blood cells containing a disease, the reading on the ammeter is minimal or near zero.

OPERATION OF THE DEVICE

The device is first set in operation by turning the voltage selector knob 9 to 21 volts and the rheostat 10 to the right. Then the power control switch 11 is turned to the "ON" position. The patient is then instructed to touch the sockets with his/her forefingers-left forefinger to the red socket and right forefinger to the black socket. If the indicator on the ammeter stays on zero the patient is normal. However, if the indicator moves away further from zero, the patient has organ malfunction.

To search for the defective or malfunctioning organ the set is adjusted with the voltage selector switch at 12 volts. Then the red plug of the terminal electrode is plugged to the red socket 4 and the black plug of the searcher electrode 8 is plugged to the black socket 5. The terminal electrode 6 is then held by the patient on the left arm while the operator probes with the rounded end of the searcher electrode 8. On the human body are acupoints connected to the organs of the body and if upon touching these points with the searcher the ammeter's indicator goes beyond 100 microamperes, such organ or organs are not functioning properly.

To stimulate properly with the apparatus, the searcher is held in place, the rounded point of the searcher electrode is held on the acupoint with the ammeter registering 100 microamperes for only 10 seconds for each acupoint. The stimulation is only 10 seconds for each acupoint in order not to harm the tissues of the body. For very young or very old persons, the time is reduced by 5 to 7 seconds with 100 microamperes of current flowing. The rheostat 10 regulates the current and allows the meter to read 100 micro-amperes during the stimulation.

Having fully described by invention, what I claim and desire to be protected by a Letter Patent is:

1. An electro-therapy apparatus for detecting malfunction of body organs via the autonomous nervous system, comprising, in combination, a transistorized oscillator-audio amplifier stage including an output transformer operative for dissipating the energy of the oscillator-audio amplifier stage, including an oscillator and audio-amplifier transistor connected to the output transformer and means for feeding back to the base of the transistor a feedback voltage derived from the voltage across the output transformer to cause the oscillator and audio-amplifier transistor to oscillate at a predetermined basic frequency dependent upon the time-constant of the feedback network of the stage; biasing network means for applying biasing voltage to the oscillator-audio amplifier stage; triggering stage means coupled to the biasing network means and operative for varying the biasing voltage thereof, the triggering stage means including a bias voltage network and a series of batteries connected thereto and supplying energy thereto; a speaker connected across the output of the output transformer; a pair of electrode jacks connected to the bias voltage network of the triggering stage means, a fixed resistor and an ammeter both connected to the bias voltage network of the triggering stage means; and a pair of electrodes removably connected to the electrode jacks and adapted to be placed upon the surface of the human body for establishing a flow of current in the triggering stage means when contacting an electropermeable location on the surface of the human body.

2. The electro-therapy apparatus defined in claim 1, wherein the predetermined basic frequency of the oscillator-audio amplifier stage is within the range between fifty and seventy cycles per second.

3. The electro-therapy apparatus defined in claim 1, the electrode jacks and the electrodes removably connected thereto being connected in series with the components of the bias voltage network of the triggering stage means.

4. An electro-therapy apparatus, comprising, in combination, an output transformer including a primary winding having first and second terminals and a center tap and a secondary having first and second terminals; a speaker having two input terminals of which one is connected to the first terminal of the secondary winding; a double-pole switch having a first contact connecting the other terminal of the speaker to the second terminal of the secondary winding and having a second contact; an oscillator transistor having a base, a collector and an emitter; a capacitor connecting the center tap to the emitter; a capacitor connected directly across the first and second terminals of the primary winding; a capacitor connecting the first terminal of the primary winding to the base of the oscillator transistor, the collector thereof being directly connected to the second terminal of the primary winding; a biasing resistor connected directly between the base and collector of the oscillator transistor; a triggering transistor having a base, a collector and an emitter; a resistor connecting the collector of the triggering transistor to the base of the oscillator transistor; a resistor and a by-pass capacitor each connected directly between the collector of the triggering transistor and the emitter of the oscillator transistor; a biasing resistor connected directly between the base of the triggering transistor and the emitter of the oscillator transistor; four batteries connected in series, the group of four batteries having first and second end terminals and first, second and third intermediate terminals, the first end terminal being connected to the emitter of the triggering transistor, the second contact of the double-pole switch connecting the emitter of the triggering transistor to the center tap of the primary winding, the first intermediate terminal being directly connected to the emitter of the oscillator transistor; a three position switch having three stationary contacts respectively connected to the second and third intermediate terminals and the second end terminal of the group of batteries and including a moving switch arm movable from one to the next of the three stationary contacts; a rheostat comprising a rheostat resistor having two end terminals one of which is connected to the moving switch arm of the three position switch and the other of which is unconnected to the remainder of the circuit and including a rheostat wiper; an ammeter having a first terminal connected directly to the base of the triggering transistor and having a second terminal; a capacitor connected directly across the first and second terminals of the ammeter; a first socket electrically connected to the second terminal of the ammeter; a second socket electrically connected to the wiper of the rheostat; a terminal electrode removably connected to the first socket; a searcher electrode removably connected to the second socket; the electro-therapy apparatus furthermore including a folding suitcase, the circuitry defined above being located within the folding suitcase, the folding suitcase being provided with a control panel, the first and second sockets being accessible through the control panel; further including three control knobs on the control panel respectively coupled to and controlling the double-pole switch, the three position switch and the rheostat wiper, the ammeter including a dial provided on the front of the control panel.

* * * * *